United States Patent
Klein

(10) Patent No.: US 6,697,161 B2
(45) Date of Patent: Feb. 24, 2004

(54) OPTICAL CHARACTERIZATION OF RETARDING DEVICES

(75) Inventor: Susanne Klein, Bristol (GB)

(73) Assignee: Hewlett-Packard Development Company, L.P., Houston, TX (US)

(*) Notice: Subject to any disclaimer, the term of this patent is extended or adjusted under 35 U.S.C. 154(b) by 58 days.

(21) Appl. No.: 10/040,425

(22) Filed: Jan. 10, 2002

(65) Prior Publication Data

US 2002/0159069 A1 Oct. 31, 2002

(30) Foreign Application Priority Data

Jan. 12, 2001 (GB) ............................................ 0100819

(51) Int. Cl.$^7$ ................................................ G01B 9/02
(52) U.S. Cl. ................................................ 356/491
(58) Field of Search ............................... 356/483, 491, 356/364, 365, 369

(56) References Cited

U.S. PATENT DOCUMENTS

| | | | | |
|---|---|---|---|---|
| 3,692,385 A | * | 9/1972 | Gievers | 359/247 |
| 4,801,798 A | | 1/1989 | Lange | 250/255 |
| 5,235,404 A | | 8/1993 | Fejer et al. | 356/351 |
| 5,257,092 A | | 10/1993 | Noguchi et al. | 356/367 |
| 5,619,325 A | | 4/1997 | Yoshida | 356/351 |

FOREIGN PATENT DOCUMENTS

EP  0 597 390  5/1994

OTHER PUBLICATIONS

Stolber et al., "Crystal Identification with the Polarizing Microscope," Chapman & Hall, pp. 30–135, Aug. 9, 1996.
Warenghem et al., "Scanning Conoscopy: A Novel Method for Studying Birefringment Samples," Mol. Cryst., Gordon and Breach Science Publishers S.A., Vol. 159, pp. 15–25, 1988.
Wahlstrom, "Optical Crystallography," 5$^{th}$ Edition, John Wiley and Sons, pp. 376–419.
Kliger et al, "Polarized Light in Optics and Spectroscopy," Academic Press, Inc., pp. 75–85.
Liu et al., "Corner–Cube Four–Detector Photopolarimeter," Optics & Laser Technology, Elsevier, vol. 29, No. 5, pp. 233–238, 1997.
Yang et al., "Guided Modes and Related Optical Techniques in Liquid Crystal Alignment Studies," The Optics of Thermotropic Liquid Crystals, Taylor & Francis Inc., pp. 85–114, 1998.

(List continued on next page.)

Primary Examiner—Samuel A. Turner
Assistant Examiner—Michael A. Lyons
(74) Attorney, Agent, or Firm—Foley & Lardner

(57) ABSTRACT

The present invention relates to the measurement of birefringence, particularly the optical characterization of retardation and eigenpolarization of an unknown retarding device (22). An optical probe beam (24) with a predetermined polarization (28) is split into two components (31,32), with constant dynamic phase difference. The beam components (31,32) pass through the retarding device (22) in opposite directions so that the polarization of each probe beam component (131,132) is retarded by an equal degree. Then, the retarded probe beam components (131,132) together pass through a polarizing analyzer (45) with a pre-determined polarization axis to resolve the polarization of each retarded probe beam component (131,132) along said axis. The polarization resolved beams (231,232) combine on an optical detector (50) so that the beams maintain the same dynamic phase and interfere coherently depending on the geometric phase between the two beams (231,232). The analyzer (45) is rotated to resolve the polarization of each of the polarization resolved beams (131,132) along its rotating axis, in order to vary the geometric phase and hence the measured interference from the detector (50). The measured varying interference is used to calculate the retardation and eigenpolarization of the retarding device (22).

12 Claims, 6 Drawing Sheets

OTHER PUBLICATIONS

Ramaseshan et al., "The Interference of Polarized Light as an Early Example of Berry's Phase," Current Science, vol. 55, No. 24, Dec. 20, 1986, pp. 1225–1226.

Pancharatnam, "Generalized Theory of Interference, and its Applications," The Proceedings of the Indian Academy of Science, vol. XLIV, No. 5, 1956, pp. 247–262.

* cited by examiner

X,Y LABORATORY SYSTEM
$X_i, Y_i$ PRINCIPAL AXES SYSTEM
Z PROPAGATION DIRECTION $$\tan\left(\frac{\theta}{2}-\frac{\pi}{4}\right) = \frac{-b}{a} \text{ LEFT}$$

$$\tan\left(\frac{\theta}{2}-\frac{\pi}{4}\right) = \frac{+b}{a} \text{ RIGHT}$$

OPTICAL CHARACTERIZATION OF RETARDING DEVICES

The present invention relates to the measurement of birefringence, particularly the optical characterization of retardation and eigenpolarization of an unknown retarding device.

The optical characterization of retarding devices, sometimes referred to as birefringent devices, is a well-known problem in crystal optics. An important area where such characterization is needed is in the field of liquid crystals. A retarding device is fully characterized when the state of polarization of light passing through the device can be predicted as a function of the state of polarization incident onto the device and as a function of the eigenpolarization and retardation of the retarding device itself. The main task is to determine the eigenpolarization and the retardation of the retarding device experimentally.

There are numerous solutions for this problem with different problems and restrictions. They can be split into three families: the family of conoscopic methods; the family of Stokes parameter methods; and the family of liquid crystal waveguide methods.

In one family of conoscopic methods of characterization, light of a known polarization is sent through the retarding device sample and the changes of polarization as a function of the direction of the light beam are analyzed by a fixed analyzer. Such methods include the classical conoscopic method (see R. E. Stoiber, *Crystal Identification with the polarizing microscope*, Chapman & Hall, New York, 1994), the scanning conoscopic method (see Warenghem, M. & Grover, C. P., *Scanning conoscopy: a novel method for birefringent samples*, Molecular Crystal and Liquid Crystal, 1988, vol. 159, pp. 15–25), and the crystal rotation method (see E. E. Wahlstrom, *Optical crystallography*, Wiley, 1979). In another family of conoscopic methods, light of known polarization is sent through the retarding device and the changes of polarization as a function of the wavelength are analyzed by a fixed analyzer. Changes in polarization result in an intensity signal which is then quantified or recorded by some means, for example by naked eye, photographic camera, or with a photodetector. These methods do not work for all kinds of retarding device. If the retarding device is below a certain thickness, the intensity signal shows too little variation and the results for the eigenpolarization and the retardation will be associated with huge error bars. For example, in the case of a liquid crystal, the sample thickness must be thicker than 10 $\mu$m. In general, conoscopic methods are not applied to retarding devices with complicated internal structures, for example twisted nematic liquid crystals.

With Stokes parameter methods of characterization, light of a known polarization is sent through the retarding device and the change of polarization is analyzed by a set of measurements with different polarizers. The classic method (see D. S. Kliger et al., *Polarized light in optics and spectroscopy*, Academic Press, Boston, 1990) requires six measurements with a linear analyzer at 0° (horizontal), 90° (vertical), 45°, 135°, and also with a right-handed circular polarizer and a left-handed circular polarizer. Almost all realizations of Stokes parameter measurements are relatively slow and cannot be adapted for real-time measurements. The newest implementation of a Stokes parameter measurement (see Liu, J., Azzam, R. M. A., *Corner-cube four-detector photopolarimeter*, Optics and Laser Technology, 1997, vol. 29, pp. 233–238) exploits the Brewster angle and does allow, for the first time, real-time measurements. But all such methods suffer from the limitation of being are very sensitive to misalignments. Therefore, the accuracy of the results is either not very high or the data collection time is long.

The liquid crystal waveguide methods (see the article by Fuzi Yang et al, *Guided modes and related optical techniques in liquid crystal alignment studies*, in the publication edited by S. Elston & R. Sambles, *The optics of thermotropic liquid crystals*, Taylor & Francis, London, 1998) are the most elaborate and also produce the most exact results. However, these methods are also difficult to implement and time consuming to perform. Sometimes, these require a specially modified sample, but always involve a complicated and time-consuming calculations for fitting data to equations describing the method.

It is an object of the present invention to provide a more convenient device and method for optically characterizing the retardation and eigenpolarization of an unknown birefringent sample.

According to the invention, there is provided a method of optically characterizing the retardation and eigenpolarization of an unknown retarding device, comprising the steps of:

a) generating an optical probe beam with a pre-determined polarization;
b) splitting the probe beam into two components, with constant dynamic phase difference;
c) passing each of the two probe beam components through the retarding device in opposite directions so that the polarization of each probe beam component is retarded by an equal degree, but the directions of the optic axis have opposite signs for the two probe beams.
d) passing the retarded probe beam components together through a polarizing analyzer with a pre-determined polarization axis to resolve the polarization of each retarded probe beam component along said axis;
e) receiving the polarization resolved beams on an optical detector so that said beams maintain the same dynamic phase and interfere coherently depending on the geometric phase between the two interfering polarization resolved beams; and
f) using the detector to measure the interference between the two interfering polarization resolved beams;

wherein the angle of the polarization axis of the analyzer is rotated to resolve the polarization of each of the polarization resolved beams along said rotating axis, in order to vary the geometric phase and hence the measured interference from the detector, the measured varying interference being used to calculate the retardation and eigenpolarisation of the unknown retarding device.

Also according to the invention, there is provided an apparatus for optically characterizing the retardation and eigenpolarization of an unknown retarding device, comprising:

a) an optical source for generating an optical probe beam with a pre-determined polarization;
b) a beam splitter for splitting the probe beam into two components, with constant dynamic phase difference between the components, the retarding device being arranged to receive from opposite directions each of the two probe beam components so that the polarization of each probe beam component is retarded by an equal degree;
d) a polarizing analyzer arranged to receive both the retarded probe beam components, the analyzer having a pre-determined polarization axis to resolve the polarization of each of the retarded probe beam components along said axis;

e) an optical detector arranged to receive the polarisation resolved beams so that said beams maintain the same dynamic phase and interfere coherently depending on a different geometric phase between the two polarization resolved beams, and to measure therefrom said interference;
f) means for rotating the angle of the polarization axis of the analyzer to resolve the polarization of each beam along said rotating axis and to vary the geometric phase between the two polarization resolved beams;

wherein the apparatus includes means for rotating the angle of the polarization axis of the analyzer to resolve the polarization of each of the polarization resolved beams along said rotating axis, in order to vary the geometric phase and hence the measured interference from the detector, the measured varying interference being used by a processor to calculate the retardation and eigenpolarisation of the unknown retarding device.

The concept of the "geometric phase" is best understood with reference to the Poincaré sphere, and will be further described in the description relating to the drawings.

Although the two probe beam components pass through the retarding device in opposite directions so that the polarization of each probe beam component is retarded by an equal degree, the directions of the optic axis for the two beams have opposite signs.

In a preferred embodiment of the invention, the measured varying interference is fit to a mathematical model of the interference between the polarization resolved beams resulting from the varying geometric phase in order to deduce the retardation and eigenpolarisation of the unknown retarding device.

It is advantageous if the method is performed using a ring interferometer. The retarding device can then be positioned in the ring, with the two probe beam components circulating around the ring and through the retarding device in opposite directions. This arrangement helps to ensure that the dynamic phase for each of the components is the same, so that essentially only the geometric phase contributes to the interference measured on the detector.

Preferably, the optical probe beam enters the interferometer through an entrance polarizer with a predetermined optical axis. The probe beam is then split by a beam splitter into said two components. The beam splitter can also be arranged to direct each component around the ring in opposite directions. After passing through and being retarded by the unknown retarding device, the two retarded probe beam components are then recombined and directed out of the ring towards the polarizing analyzer. Such an arrangement uses a small number of optical components, and is relatively inexpensive to construct and operate.

One way to form a ring interferometer is with a plurality of plane mirrors. In order to minimize polarization shifts polarization-preserving components are used and the predetermined polarisation in the entrance of the interferometer is either horizontal or vertical.

The invention will now be described in further detail, and by way of example with reference to the accompanying drawings, in which.

Figure 3:
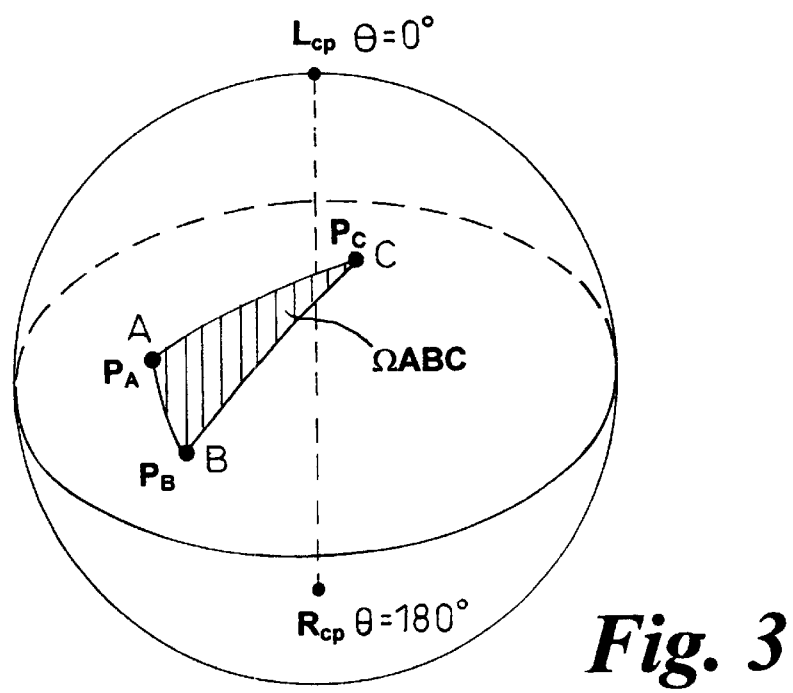
FIG. 3 is a drawing of a Poincaré sphere, illustrating the concept of a geometric phase when two input polarized beams are resolved by a polarizing element.
Figure 8:
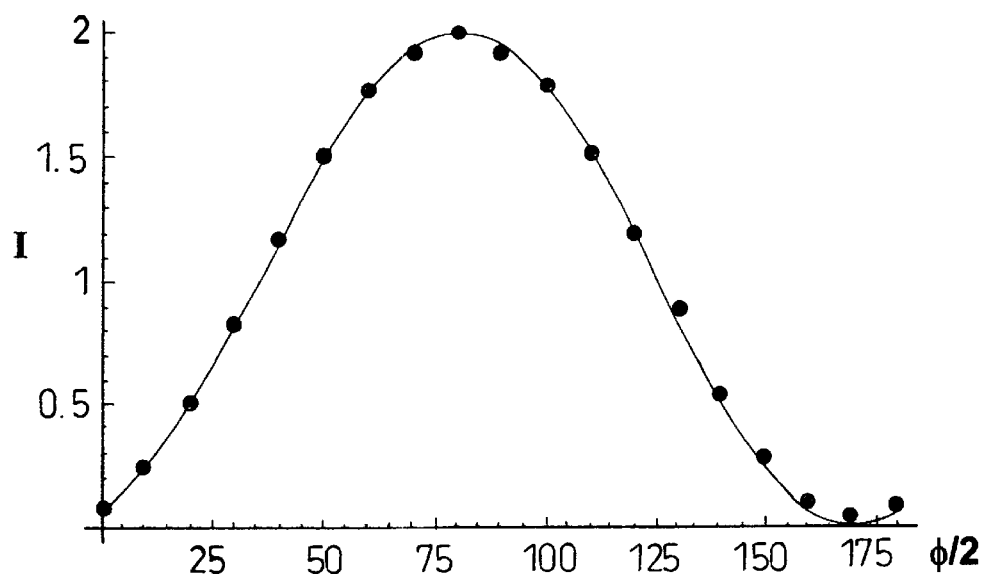
Figure 9:
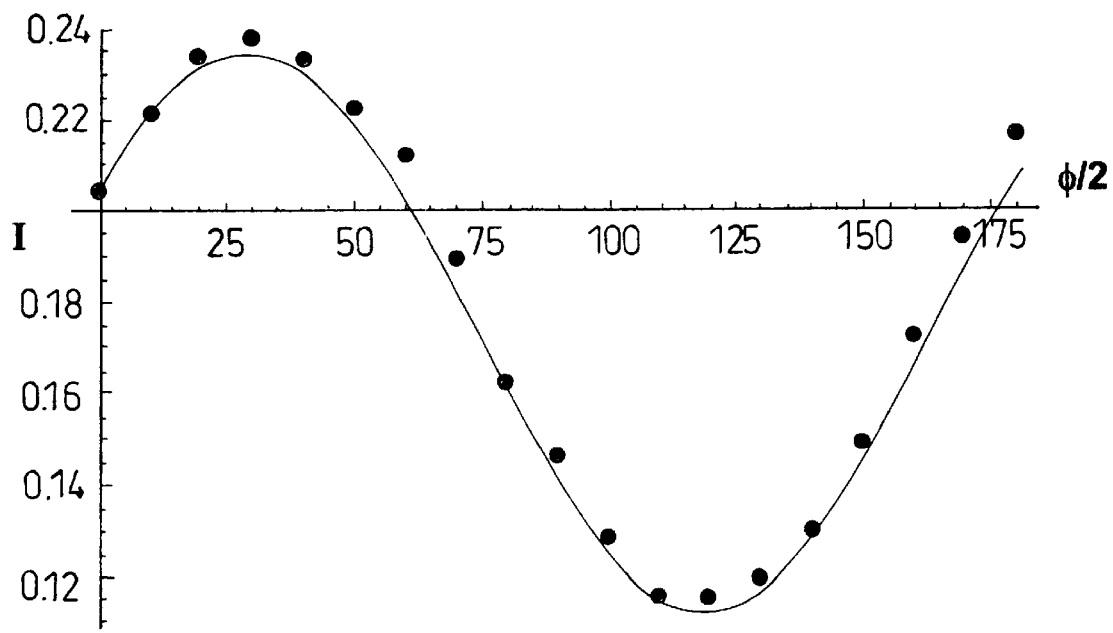

FIG. 8 shows a calibration plot of normalized intensity against analyzer angle for the apparatus of FIG. 3, when a known quarter-wave plate is used in place of the unknown retarding device in order to reduce systematic errors prior to characterizing the retardation and eigenpolarization of an unknown retarding device; and FIG. 9 shows a plot of normalized intensity against analyzer angle for the apparatus of FIG. 3, showing how this is initially calibrated in order to reduce systematic errors prior to characterizing the retardation and eigenpolarization of an unknown retarding device.

Figure 1A:
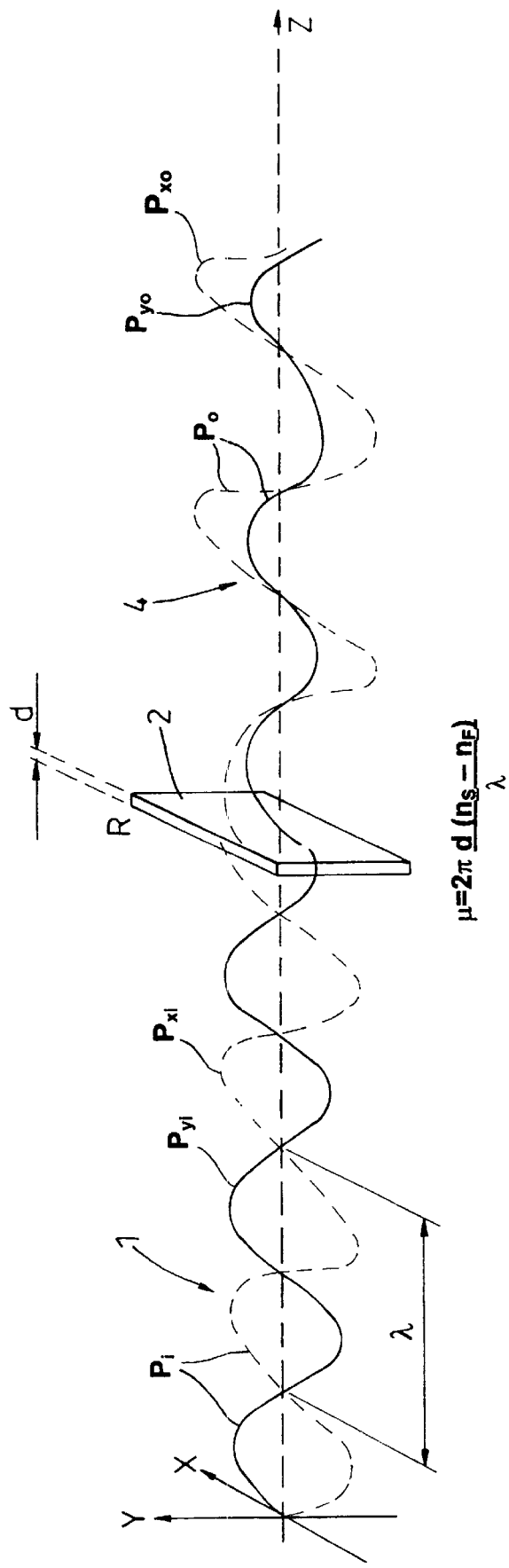
FIGS. 1A to 1D are a drawings illustrating changes in polarization as generally polarized optical input beam passes through a general optical retarding device.

FIG. 1A is a drawing in a "laboratory" Cartesian coordinate system (x,y,z) of a generally polarized optical input probe beam 1 of wavelength $\lambda$ that travels along the z-axis passing through a general optical retarding device (R) 2 having a physical thickness d. The input beam 2 has an input polarization $P_i$ that can be resolved into orthogonal components along the x-axis and the y-axis as $P_{xi}$ and $P_{yi}$. When the device is uniaxial any particular wave normal direction can be resolved into an ordinary wave, with a velocity $c/n_o$ independent of the direction of propagation, and into an extraordinary wave with the velocity $c/n_e$ depending on the angle between the direction of the wave normal and the optic axis. The two velocities are only equal when the wave normal is in the direction of the optic axis. The phase difference introduced by such a device is $$\mu = 2\pi d(n_e - n_o)/\lambda. \tag{1}$$

In general, the retardation angle g may be between $-360° \leq \mu \leq 360°$.

The output beam 4 then has an output polarization $P_o$ that will usually be different from that of the input polarization $P_i$, and which can be resolved into orthogonal components along x and y axes as $P_{xo}$ and $P_{yo}$.

Figure 1B:
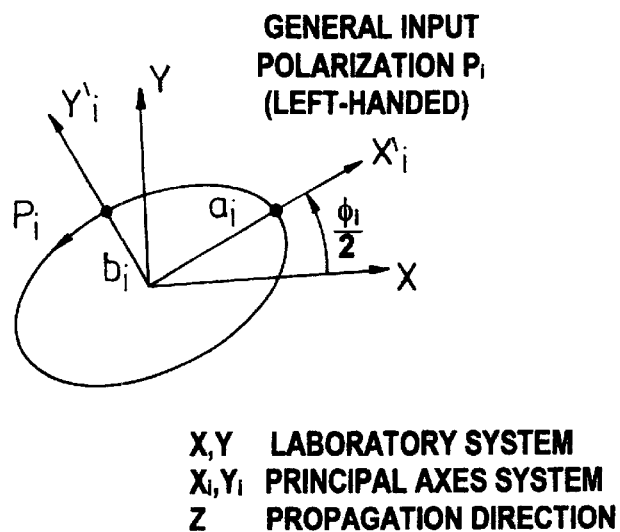
Figure 1C:
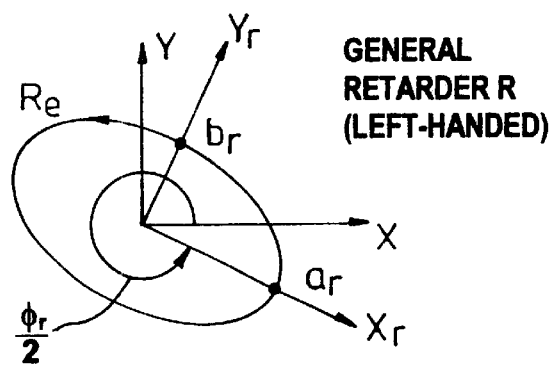
Figure 1D:
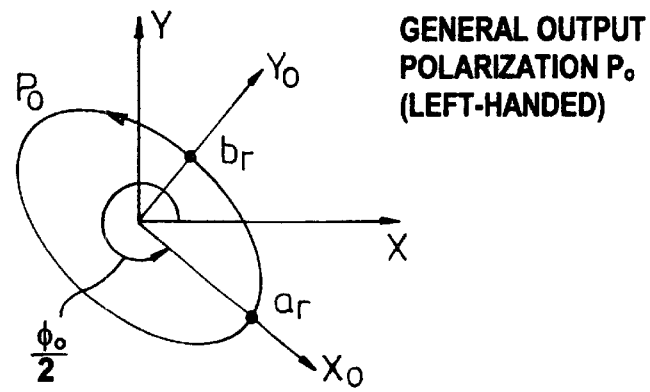

FIGS. 1B, 1C and 1D show views along the z-axis of, respectively, the input polarization $P_i$, the eigenpolarization $R_e$ of the retarding device 2, and the output polarization $P_o$ These polarization may be linear, circular of elliptical, but the elliptical case is shown for generality. Also for generality, the major and minor axes $(x_i,y_i)$ of the elliptically polarized input beam $P_i$ are shifted by an input polarization angle $\Phi_i/2$ with respect to the laboratory axes (x,y). Similarly, the major and minor axes $(x_o,y_o)$ of the elliptically polarized output beam $P_i$ are shifted by an angle $\Phi_o/2$ with respect to the laboratory axes (x,y).

The retarding device is shown having an elliptical eigenpolarization $R_e$, as would be the case with retarding device such as twisted nematic or cholesteric liquid crystal cells. Again, for generality, the major and minor axes $(x_r,y_r)$ axes of the eigenpolarization Re are shifted by a retarding device angle $\Phi_r/2$ with respect to the laboratory axes (x,y).

Figure 2:
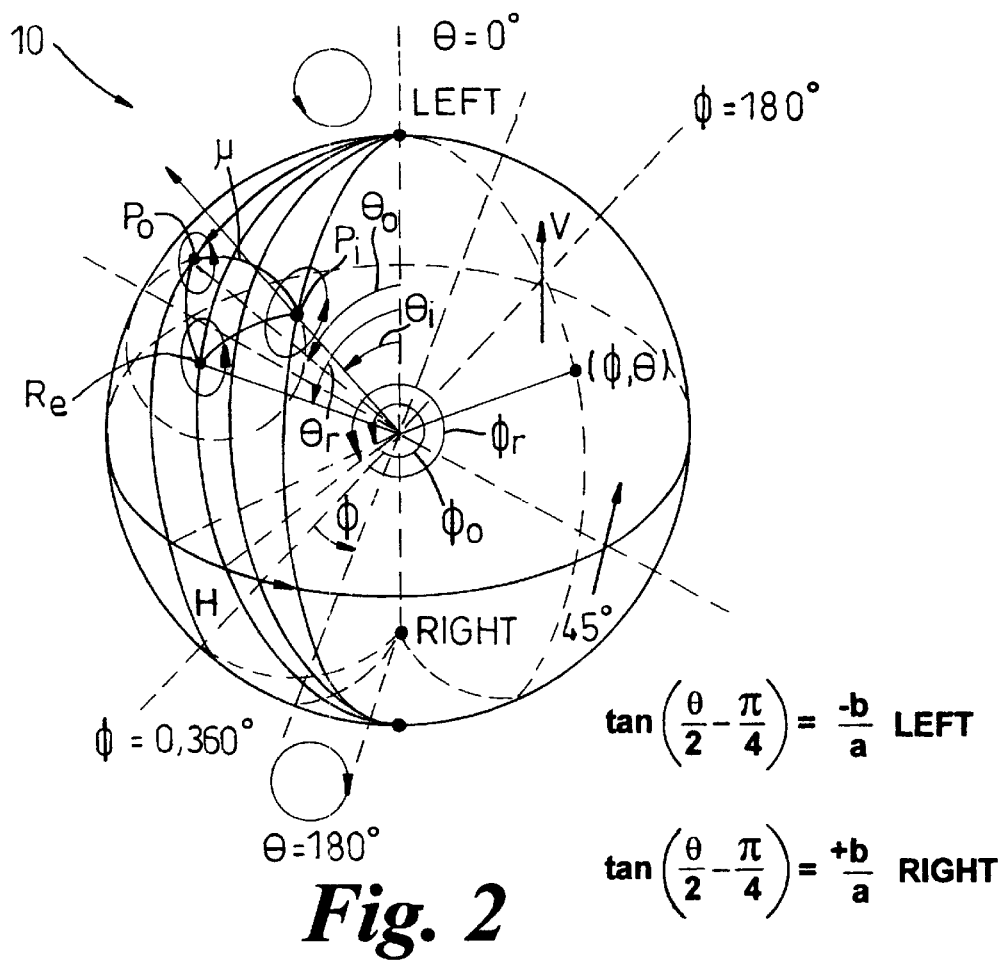
FIG. 2 is a drawing of a Poincaré sphere, showing how this can be used to describe the eigenpolarization and retardation of the retarding device for and polarization change of the optical beam in FIG. 1.

FIG. 2 is a drawing of a Poincaré sphere 10, showing how this can be used to describe the eigenpolarization $R_e$, and retardation of the retarding device 2, and the polarization shift this device creates between the input beam 1 and output beam 4. Any state of polarization can be mapped onto a point on the surface of the sphere, the coordinates of which can be written in polar notation as ($\Phi,\theta$), where $\Phi$ the polarization state is horizontally oriented along the x-axis is an equatorial angle, and $\theta$ is an azimuthal angle, such that $0 \leq \Phi \leq 360°$ and $0 \leq \theta \leq 180°$. Points on the equator represent states of linear polarization, the north pole represents left circular polarization, and the south pole represents right circular polarization. Points in between the equator and poles represent all the different possible states of elliptical polarization. At $\Phi=0°$, the polarization state is horizontally oriented along the laboratory x-axis, and at $\Phi=180°$ the polarization state is vertically oriented along the laboratory y-axis. The angle $\Phi$ is therefore the angle of the polarization.

On the Poincaré sphere the input polarization $P_i$ is defined by the angles ($\Phi_i,\theta_i$) the output polarization $P_o$ is defined by the angles ($\Phi_o,\theta_o$) and the eigenpolarization $R_e$ of the retarding device 2 is defined by the angles ($\Phi_r,\theta_r$).

The input polarization angle $\theta_i$ is related to the major diameter $a_i$ and minor diameters $b_i$ of the input polarization ellipse $P_i$ shown in FIG. 1B by the equation $$\tan\left(\frac{\theta_i}{2} - \frac{\pi}{4}\right) = \frac{b_i}{a_i}.$$

The output polarization angle $\theta_o$ is related to the major diameter $a_o$ and minor diameters $b_o$ of the output polarization ellipse $P_o$ shown in FIG. 1D by the equation $$\tan\left(\frac{\theta_0}{2} - \frac{\pi}{4}\right) = \frac{b_0}{a_0}.$$

Similarly, the retarding device angle $\theta_r$ is related to the major diameter $a_r$ and minor diameters $b_r$ of the retarding device ellipse $R_e$ shown in FIG. 1C by the equation $$\tan\left(\frac{\theta_r}{2} - \frac{\pi}{4}\right) = \frac{b_r}{a_r}.$$

The angle $\theta$ is therefore a function of the ellipticity of the polarization.

A interesting property of the Poincaré sphere is that when an input light beam 1 of polarization ($\Phi_i,\theta_i$) enters a retarding device 2 of eigenpolarization ($\Phi_r,\theta_r$), the initial polarization of the light beam develops along an arc of a circle on the surface of the Poincaré sphere starting at the point ($\Phi_i,\theta_i$) and centered on the point ($\Phi_r,\theta_r$). When the light beam exits the retarding device 2, the arc has subtended an angle equal to the angle $\mu$ defined by equation (1), which is referred to as the retardation of the retarding device 2.

A further interesting property of the Poincaré sphere was discovered by S. Pancharatnam in 1956 (S. Pancharatnam; *Generalized Theory of Interference and its Applications*; Proc. Ind. Acad. Sci. A 44 247–262 (1956)). This property, referred to now as "Pancharatnam's phase", was unfortunately was neglected by the scientific community until its connection with Berry's phase was found in 1986 (S. Ramaseshan, R. Nityananda; *The interference of polarized light as an early example of Berry's phase*; Current Science India 55 1225–126 (1986))

With reference now to FIG. 3, which shows three points A, B and C on the surface of a Poincaré sphere, Pancharatnam discovered that if two polarized light beams of intensity $I_A$ and $I_B$, and with polarizations $P_A$ and $P_B$ enter a polarizing device with eigenpolarization $P_C$, then the resultant intensity I of the light beam exiting the retarding device is given by the equation:

$$I = I_A + I_B + 2\sqrt{I_A I_B} \cos\left(\frac{1}{2} AB\right) \cos\left(\delta + \frac{1}{2}\Omega_{ABC}\right) \quad (2)$$

where:
$A_B$ is a the length of an arc between point A and B
$\delta$ is the dynamic phase difference between the two beams
$\Omega_{ABC}$ is the spherical excess (i.e. the area) of the spherical triangle ABC The parameter $\Omega/2$ is the "geometric phase". As will be explained below, the geometric phase $\Omega/2$ is a function of the orientation of the analyser 45, the eigenpolarisation ($\Phi,\theta$) and the retardation $\mu$ of the retarding device 22.

Figure 4:
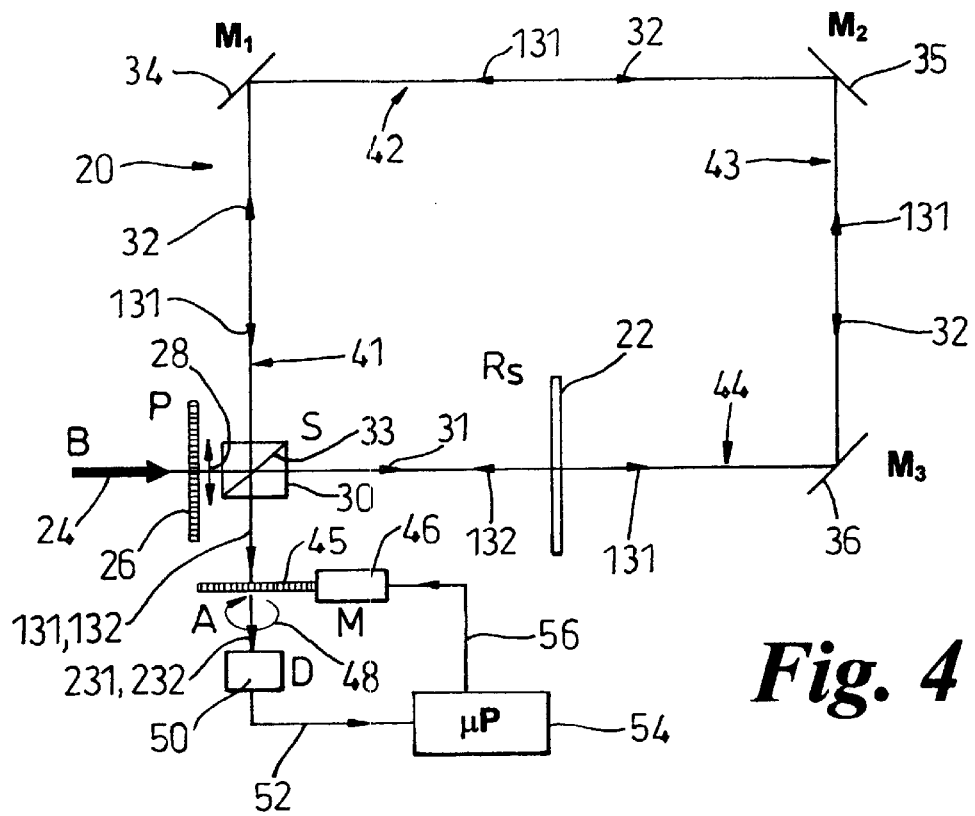
FIG. 4 is a drawing of an apparatus according to the invention for optically characterizing the retardation and eigenpolarization of an unknown retarding device.
Figure 5:
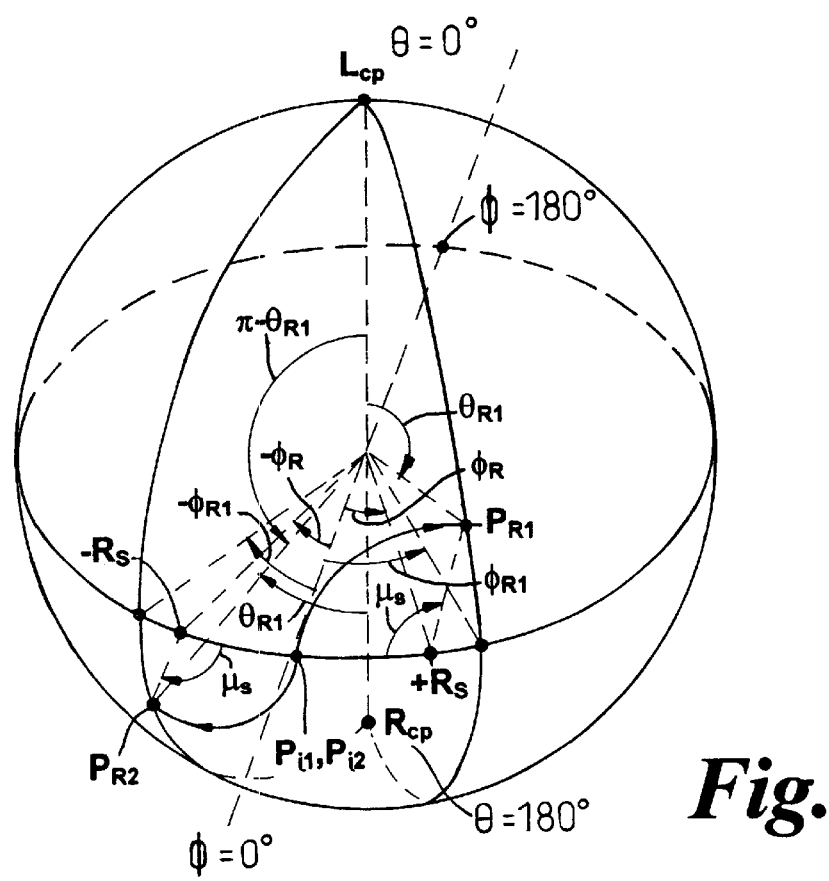
FIGS. 5 and 6 are drawings of a Poincaré sphere, showing how for the apparatus of FIG. 3, the geometric phase can be used to characterize the retardation and eigenpolarization of an unknown retarding device having a non-elliptical eigenpolarisation.

As can be seen from FIG. 5, for one of the probe beam components, $\Phi_r/2$ is the orientation of the optical axis of the retarding device relative to the polarization of said probe beam component and $$\chi_r = \frac{\theta_r}{2} - \frac{\pi}{4}$$

is the ellipticity of the optical axis of the retarding device for said component; and The invention will now be described with reference to FIGS. 4 to 9. FIG. 4 shows a drawing of an apparatus 20 for optically characterizing the retardation $\mu$ and eigenpolarization ($\Phi_r,\theta_r$) of an unknown retarding device $R_S$22.

The apparatus 20 receives an input unpolarized light beam B 24. This passes through an input polarizer P 26 that passes only light that is linearly polarized 28 in the plane of the drawing. The linearly polarized light 28 enters a beam splitter cube S 30 that divides the input polarized light 28 into two components 31,32, one of which 31 passes straight through the splitter cube 30, and the other of which 32 is reflected at 90° by an internal 45° interface 33 within the cube 30. The beam splitter 30 maintains the polarization of the beam components 31,32.

The two components 31,32 are displaced by three mirrors M1 34, $M_2$ 35, and $M_3$ 36, which together with the beam splitter cube 30 are positioned at the corners of a square or rectangle. The arrangement is therefore that of a ring interferometer with four arms 41,42,43,44 in which the components 31,32 overlap and circulate in opposite directions.

The retarding device 22 is located in one arm 44 (it matters not which arm) so that the beam components 31,32 pass through the retarding device in opposite directions. The retarding device will alter, or "retard" the polarization of the components so that after passing through the retarding device 22, the circulating light becomes retarded components 131,132, after one complete circuit of the ring are recombined by the beam splitter cube 30, which again does not alter the polarization of the retarded components 131, 132, which are then directed out of the ring and towards a polarizing analyzer A 45.

For convenience, the polarizing analyzer 45 is a linear polarizing device, so that the polarization of each of the retarded beam components 131,132 is resolved into two resolved beam components 231,232 along a linear direction determined by the orientation of the analyzer 45.

The orientation of the analyzer 45 is variable, and is changed by a motor M 46 arranged to rotate 48 the polarizing axis of the analyzer 45, preferably around at least 360° around a direction defined by the propagation axis of the combined retarded beam components 131,132.

The analyzer passes a beam consisting of the two resolved components 231,232 towards a photodetector D 50, that converts the intensity of the resolved components 231,232 into an electrical signal 52, that is received by a processing means μP 54, such as a microcomputer. The microcomputer also provides an output signal 56 to the motor 46 to control the angular orientation of the analyzer 45.

Figure 6:
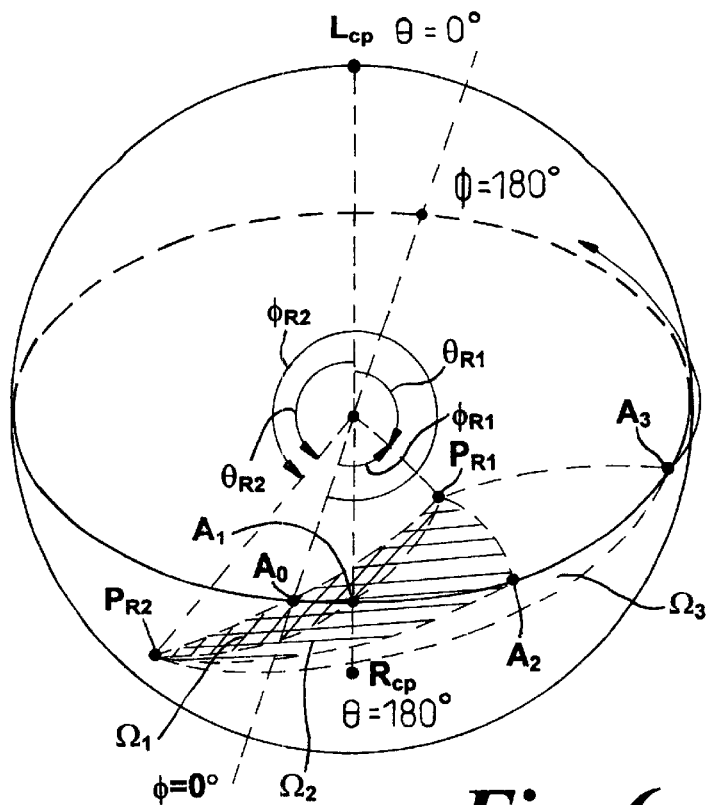

The polarization of the light as it passes through the apparatus 20 towards the detector 50 can now be plotted on a Poincaré sphere, illustrated for clarity in two stages in FIGS. 5 and 6.

In FIG. 5, point $P_{i1}$ and $P_{i2}$ are the superimposed, identical polarization states of the two beam components 31,32 output by the beam splitter cube 30. The polarization states are in the plane of the page, which in a conveniently constructed apparatus would correspond with a horizontal polarization. The angle $\Phi_i$ of the polarization for the initial beam components $P_{i1}$ and $P_{i2}$ 31,32 is therefore zero.

The initial beam components 31,32 pass though the retarding device 22 in opposite directions, and so in the co-ordinate system of one beam 31, the eigenpolarization of the retarding device 22 is $+R_S$, and the co-ordinate system of the other beam 32, the eigenpolarization of the retarding device 22 is $-R_S$. In FIG. 5, the retarding device 22 eigenpolarization is shown having a non-zero polarization angle ($\Phi_R$ for one beam component 31, and $-\Phi_R$ for the other beam component 32), but for simplicity an ellipticity θ of 90°, which in the defined co-ordinates is zero ellipticity, or linear. The point $+R_S$ is therefore defined by the point ($\Phi_R$, 90°) and the point $-R_S$ is defined by the point ($-\Phi_R$, 90°).

The retarding device 22 alters the polarization of the two oppositely directed beam components 31,32 by rotating the point $P_{i1}$ of one beam component 31 about the point $+R_S$ by an angle $\mu_S$ to point $P_{R1}$ and by rotating the point $P_{i2}$ of the other beam component 32 about the point $-R_S$ by the same angle $\mu_S$ to point $P_{R2}$. As explained above, this rotation angle $\mu_S$ is the retardation of the retarding device 22.

The retarded beam components 131,132 are then recombined by the beam splitter cube 30, which does not change the points $P_{R1}$ and $P_{R2}$ for the retarded beam components 131,132.

The effect of the analyzer is shown in FIG. 6. The analyzer for convenience may initially be oriented with its polarization axis in the plane of the drawing, that is, horizontal with a polarization angle $\Phi_A$=0°. The analyzer will resolve the retarded beam components 131,132 into corresponding resolved beam components 231,232, which then combine on the detector 50. This initial analyzer setting $\Phi_A$=0° is represented by point $A_0$ in FIG. 6. Because of the symmetry of this special case, the points $P_{R1}$, $A_0$ and $P_{R2}$ all lie on an arc of a great circle, and so the triangular area $\Omega_0$ defined by these points is zero. When the interferometer is in destructive interference mode, δ=π, the intensity of the light on the detector 50 will also be zero. Energy is conserved and constructive interference occurs into the direction of the source.

Figure 7:
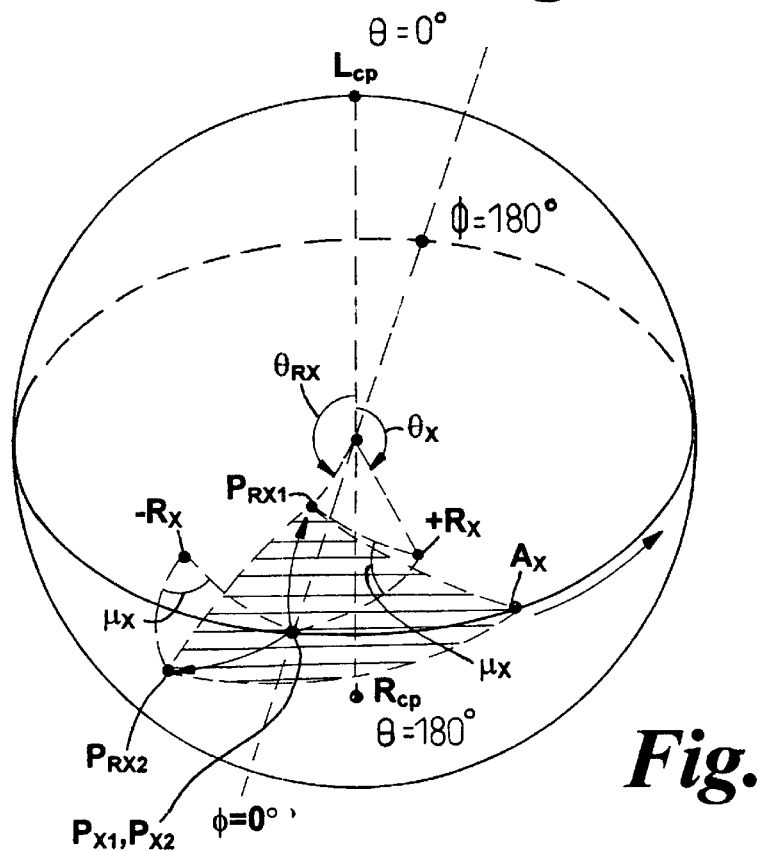
FIG. 7 is a drawing of a Poincaré sphere similar to that of FIGS. 5 and 6, showing how for the apparatus of FIG. 3, the geometric phase can be used to characterize the retardation and eigenpolarization of an unknown retarding device having an elliptical eigenpolarisation.

As shown in FIG. 7, the analyzer 45 is then rotated by the motor 48 under the control of the processor 54, so that the analyzer polarization axis passes through point $A_1$, $A_2$, $A_3$, etc around the equator of the Poincaré sphere. Here, the polarization of the analyzer 45 is defined by the parameter ($\Phi_A$, 0) on the Poincaré sphere, where $0 \leq \Phi_A \leq 360°$ and the angle $\Phi_A/2$ is the angle of the polarization axis of the analyzer 45 relative to the polarization axis of the probe beam components 31,32 prior to retardation of the polarization of each of the probe beam components 31,32 by the retarding device 22.

When the analyzer is at point $A_1$, the area of the spherical triangle defined by the points $P_{R1}$, $P_{R2}$ and $A_1$ is $\Omega_1$, at point $A_2$, the area is $\Omega_2$, and so on. As can be seen, the area Ω will increase until, in this case, the analyzer 45 is rotated to a polarization angle $\Phi_A$=180°, which corresponds to a physical angle of 90°, after where, the area Ω declines again to zero when the analyzer reaches a polarization angle $\Phi_A$=360°. The intensity detected on the detector 50 therefore follows a sinusoidal pattern as the analyzer 45 is rotated. Preferably, the polarization axis of the analyzer 45 is rotated at least by 360°.

The essence of the invention is the realization that it is possible to characterize the retardation and eigenpolarization of an unknown retarding device from such a varying signal, which depends ultimately on the variation in the geometric phase Ω/2. This is greatly facilitated by the ring interferometer arrangement, which ensures that the dynamic phase difference δ in equation (2) between the two beam components 31,32;131,132;231,232 remains constant, and the measurement takes place.

For many type of sample, in particular liquid crystal sample where the orientation of molecules is pre-determined by the preparation of the sample, it is possible to know beforehand the polarization angle Φ, which also simplifies the calculation of the eigenpolarization and retardation. It has also been found that the accuracy of the measurement can be improved if there is a good separation on the Poincaré sphere between the retarded points $P_{R1}$ and $P_{R2}$. It is therefore preferable if the polarization angle of the unknown retarding device 22 is set at $\Phi_r/2$=45° (or '45°) in the ring interferometer.

The method of calculation of the eigenpolarization and retardation of the unknown retarding device 22 will now be described.

To describe polarized light, we use spinors defined as follows. The light beam is travelling in the s-direction, and the associated electromagenetic wave depends only on z. Then the electric vector D is transverse, with complex components Dx and Dy. Defining the normalized vector by $$d = \frac{D}{(D \cdot D^*)^{1/2}} \tag{3}$$

we associate with d the spinor $$|\psi> = \frac{1}{\sqrt{2}} \begin{pmatrix} d_x + id_y \\ d_x - id_y \end{pmatrix} \tag{4}$$

i.e. the co-ordinate system of the light vector is now transformed from a linear one into a circular one. The polarization state of the light is represented by a point on the Poincaré sphere, specified by the unit vector $$r = (\sin θ \cos \phi, \sin θ \sin \phi, \cos θ). \tag{3}$$

As described above, a general point r represents elliptic polarization; an equatorial r represents linear polarization; r at the north and south poles represents left and right circular polarizations. Only completely polarized light is considered and therefore all the states of polarization lie on the surface of the Poincaré sphere. We can now write the spinor as a vector of the Poincaré sphere and adopt the convention $$|r> = \begin{pmatrix} \cos(\theta/2) \\ \sin(\theta/2)\exp(i\phi) \end{pmatrix}. \quad (4)$$

Orthogonal states of polarization fulfil the equation:

$$<r_1|r_2>=0.$$

Optical elements change the polarization r and are represented by matrices that transform the corresponding spinor. An ideal general polarizer whose axis of transmission is $r_0$ projects any incident polarisation onto $r_0$ and is represented by the projection matrix $$P(r_0) = \frac{1}{2}\begin{bmatrix} 1+\cos\theta_0 & \sin\theta_0\exp(-i\phi_0) \\ \sin\theta_0\exp(i\phi_0) & 1-\cos\theta_0 \end{bmatrix}. \quad (5)$$

An ideal retarder has orthogonal fast and slow eigenpolarizations and introduces phases $$-\frac{\mu}{2} \text{ and } +\frac{\mu}{2}$$

to them. It rotates an arbitrary polarisation by an angle $\mu$ about the axis of the fast eigenpolarisation $r_0$, and is represented by the unitary matrix:

$$R(r_0, \mu) = \begin{bmatrix} \cos\frac{\mu}{2} - i\sin\frac{\mu}{2}\cos\theta_0 & -i\sin\frac{\mu}{2}\sin\theta_0\exp(-i\phi_0) \\ -i\sin\frac{\mu}{2}\sin\theta_0\exp(i\phi_0) & \cos\frac{\mu}{2} + i\sin\frac{\mu}{2}\cos\theta_0 \end{bmatrix}. \quad (6)$$

The unknown birefringent retarding device 22 is represented by such a matrix. With the help of the concept of the geometric phase $\Omega/2$ it is possible to determine the retardation and the (fast) eigenpolarisation of the sample by a simple measurement.

Using the apparatus of FIG. 4, we generate a purely geometric phase $\Omega/2$ without obscuring it by any dynamic phase $\delta$, and from this determine the retardation g and the eigenpolarisation $(\Phi,\theta)$ of the unknown retarding device 22. When the two beam components 131,132 are recombined by the beam splitter 30, it is clear that both components have gained the same dynamic phase, i.e. the dynamic phase difference between the two components 131,132 remains constant.

The orientation of the analyser is known. The eigenpolarisation and the retardation of the retarding device 22 can be recovered from the intensity data measured by the detector 50 and recorded by the processor 54. To achieve maximal sensitivity we arrange the interferometer 20 and the detector 50 in such a way that the detector 50 is covered by a dark fringe only when the interferometer is empty and input polarizer 26 and analyzer 45 are parallel in the plane of the drawing.

For initial calibration purposes a retarding device of known eigenpolarization and retardation, such as a quarter wave plate is inserted in the ring interferometer before each set of measurements. This avoids the need to make absolute light intensity.

The formula for the detected intensity as a function of the orientation of the analyser 45 is calculated as follows:

$$I(\phi_A, \phi_R, \Delta) = \quad (7)$$
$$|P_{analyser}(\phi_A) \cdot (R(\phi_R, \frac{\pi}{2}) + R(-\phi_R, \frac{\pi}{2}) \cdot \exp[i(\pi+\Delta)]) \cdot |h>|^2$$

with $$P_{analyser}(\phi_A) = \frac{1}{2}\begin{bmatrix} 1 & \exp(-i\phi_A) \\ \exp(i\phi_A) & 1 \end{bmatrix}$$

being a linear polarizer in the exit of the interferometer at an angle, $$\frac{\phi_A}{2},$$

$$R(\phi_R, \frac{\pi}{2}) = \frac{1}{\sqrt{2}}\begin{bmatrix} 1 & -i\exp(-i\phi_R) \\ -i\exp(i\phi_R) & 1 \end{bmatrix}$$

being the calibration quarter-wave plate at $\Phi_R/2$ and $$|h> = \frac{1}{\sqrt{2}}\begin{pmatrix} 1 \\ 1 \end{pmatrix}$$

being the horizontal polarization entering the interferometer. The factor $\exp[i(\pi+\Delta)]$ describes that the port of the interferometer towards the detector shows destructive interference, which is perhaps not perfectly reached.

Then $$I(\phi_A, \phi_R, \Delta) = \frac{1}{2}(-\cos(\Delta)\cdot(1+\cos(2\phi_R)+2\cos\phi_A) + \quad (8)$$
$$2(1+\cos^2(\phi_R)\cos\phi_A + \sin\phi_R\sin\Delta\sin\phi_A))$$

In general we will orient the quarter-wave plate at 45° and then equation (8) will simplify to $$I(\phi_A, \Delta) = 2\sin^2\left(\frac{\phi_A+\Delta}{2}\right). \quad (9)$$

FIG. 8 shows a calibration curve with theoretical fit. The intensity is plotted as a function of $\Phi_A/2$.

For an unknown retarding device 22, equation (7) becomes $$I(\Phi_A,\Phi_R,\Delta,\mu,\theta)=|P_{analyser}(\Phi_A)\cdot(R(\Phi_R,\theta,\mu)=R(-\Phi_R,\theta,\mu)\cdot\exp[i(\pi=\Delta)])\cdot|h>|^2 \quad (10)$$

and equation (8) is then $$I(\phi_A, \phi_R, \Delta, \mu, \theta) = \frac{1}{4}(\cos\phi_A[1+\sin^2(\theta)-\sin^2(\phi_R)(1+\sin^2(\phi)) + \quad (11)$$
$$\cos\mu(3-\sin^2(\theta)+\sin^2(\phi_R)(1+\sin^2(\theta))) -$$
$$2\cos^2(\phi_R)\cos^2(\theta)\sin^2(\frac{\mu}{2}) + 4\cos^2(\phi_R)\sin^2(\theta)\sin^2(\frac{\mu}{2}) -$$
$$4\sin\phi_R\sin\Delta\sin(2\theta)\sin^2(\frac{\mu}{2})] -$$
$$\cos\Delta[3+\cos\mu+2\cos\phi_A+2\cos\mu\cos\phi_A-\sin^2(\phi_R) +$$
$$\cos\mu\sin^2(\phi_R)-\sin^2(\theta)+\cos\mu\sin^2(\theta) +$$
$$2\cos\phi_A\sin^2(\theta) - 2\cos\mu\cos\phi_A\sin^2(\theta) -$$

-continued $$\sin^2(\phi_R)\sin^2(\theta) + \cos\mu\sin^2(\phi_R)\sin^2(\theta) -$$

$$\cos^2(\theta)(-3 + \cos(2\phi_R) + 4\cos\phi_A)\sin^2\left(\frac{\mu}{2}\right) +$$

$$4\cos^2(\phi_R)\sin^2(\theta)\sin^2\left(\frac{\mu}{2}\right) + 4\cos\theta\sin\mu\sin\phi_A\Big] +$$

$$4\Big[1 + \cos\theta\sin\mu\sin\phi_A +$$

$$\sin\phi_R\sin\Delta\Big(\sin(2\theta)\sin^2\left(\frac{\mu}{2}\right) + \sin\theta\sin\mu\sin\phi_A\Big)\Big]\Big]$$

It can be shown that equation (11) embodies the variation of the geometric phase $\Omega/2$ and is equivalent to equation (2).

For different liquid crystal cell types we have different optimal choices for $\Phi_R$, i.e. we will get then a maximal signal.

$$\frac{\phi_A}{2}$$

is again the orientation of the analyser. The symbols $\Delta$, $\mu$, and $\theta$ are the parameters that will be fitted.

FIG. 9 shows experimental data for a twisted nematic cell and its theoretical fit.

The accuracy of the method is extremely high for the following four reasons:
1. The method is an interferometric method and produces therefore data of high accuracy.
2. Ring interferometers are very robust set ups that generate data with very little noise.
3. Rotating an analyser outside the interferometer generates the data. This guarantees that the noise generated by the measurement procedure is minimal.
4. The number of data points collected per single measurement, i.e. one full rotation of the analyser, is high. This guarantees a high accuracy.

The speed of the measurement is only dependent on the data collection speed, i.e. on the rotation speed of the analyser and the response time of the detector. For fast components the measurement time is only seconds. The set up allows even real time observation of liquid crystals switching. A suitable position of the analyser is chosen and the intensity measurement is performed. The accuracy will decrease but the measurement time is now the response time of the detector only.

What is claimed is:

1. A method of optically characterizing the retardation and eigenpolarization of an unknown retarding device, comprising the steps of:
    a) generating an optical probe beam with a pre-determined polarization;
    b) splitting the probe beam into two components, with constant dynamic phase difference;
    c) passing each of the two probe beam components through the retarding device in opposite directions so that the polarization of each probe beam component is retarded by an equal degree;
    d) passing the retarded probe beam components together through a polarizing analyzer with a pre-determined polarization axis to resolve the polarization of each retarded probe beam component along said axis;
    e) receiving the polarization resolved beams on an optical detector so that said beams maintain the same dynamic phase and interfere coherently depending on the geometric phase between the two interfering polarization resolved beams; and
    f) using the detector to measure the interference between the two interfering polarization resolved beams;
    wherein the angle of the polarization axis of the analyzer is rotated to resolve the polarization of each of the polarization resolved beams along said rotating axis, in order to vary the geometric phase and hence the measured interference from the detector, the measured varying interference being used to calculate the retardation and eigenpolarisation of the unknown retarding device.

2. A method as claimed in claim 1, in which the measured varying interference is fit to a mathematical model of the interference between the polarization resolved beams resulting from the varying geometrical phase in order to deduce the retardation and eigenpolarisation of the unknown retarding device.

3. A method as claimed in claim 1, in which the eigenpolarisation of the retarding device is defined by the parameters ($\phi_r$,$\theta_r$) on a Poincaré sphere, where $\phi_r$ is an equatorial angle, and $\theta_r$ is an azimuthal angle, such that:
    i) 0 $\phi_r$ 360° and 0 $\theta_r$ 180°;
    ii) for one of the probe beam components, $\phi_r/2$ is the orientation of the optical axis of the retarding device relative to the polarization of said probe beam component and $$\frac{\theta_R}{2} - \frac{\pi}{4}$$

the ellipticity of the optical axis of the retarding device for said component; and
    iii) for the other of the probe beam components, $-\phi_r/2$ is the orientation of the optical axis of the retarding device relative to the polarization of said probe beam component and $$\frac{\theta_R}{2} - \frac{\pi}{4}$$

is the ellipticity of the optical axis of the retarding device for said component.

4. A method as claimed in claim 3, in which said angles $-\phi_r/2$ and $\phi_r/2$ are pre-determined.

5. A method as claimed in claim 4, in which the angle $\phi_r/2$ is 45° or −45°.

6. A method as claimed in claim 1, in which the retardation of the retarding device is defined by a retardation angle $\mu$, where 0 $\mu$ 360°.

7. A method as claimed in claim 1, in which the polarization of the analyzer is defined by the parameter ($\phi_a$,$\pi/2$) on a Poincaré sphere, where 0 $\phi_A$ 360° and the angle $\phi_A/2$ is the angle of the polarization axis of the analyzer relative to the polarization axis of the probe beam components prior to retardation of the polarization of each of the probe beam components by the retarding device.

8. A method as claimed in claim 1, in which the polarization axis of the analyzer is rotated at least by 360°.

9. A method as claimed in claim 1, in which the method is performed using a ring interferometer with the retarding device in the ring, the two probe beam components circulating around the ring and through the retarding device in opposite directions.

10. A method as claimed in claim 9, in which the optical probe beam enters the interferometer through an entrance polarizer with a predetermined optical axis, the probe beam being split by a beam splitter into said two probe beam components, the beam splitter directing each component around the ring in opposite directions and then recombining and directing the probe beam components out of the ring towards the polarizing analyzer.

11. A method as claimed in claim 10, in which the ring includes a plurality of plane mirrors, the pre-determined polarization of the entrance polarizer and direction of propagation of said two probe beam components defining a plane that is normal to the plane of each mirror.

12. An apparatus for optically characterizing the retardation and eigenpolarization of an unknown retarding device, comprising:
   a) an optical source for generating an optical probe beam with a pre-determined polarization;
   b) a beam splitter for splitting the probe beam into two components, with constant dynamic phase difference between the components;
   c) a retarding device arranged to receive from opposite directions each of the two probe beam components from the beam splitter so that the polarization of each probe beam component is retarded by an equal degree;
   d) a polarizing analyzer arranged to receive both the retarded probe beam components, the analyzer having a pre-determined polarization axis to resolve the polarization of each of the retarded probe beam components along said axis;
   e) an optical detector arranged to receive the polarisation resolved beams so that said beams maintain the same dynamic phase and interfere coherently depending on a different geometric phase between the two polarization resolved beams, and to measure therefrom said interference;
   f) means for rotating the angle of the polarization axis of the analyzer to resolve the polarization of each beam along said rotating axis and to vary the geometric phase between the two polarization resolved beams;

wherein the apparatus includes means for rotating the angle of the polarization axis of the analyzer to resolve the polarization of each of the polarization resolved beams along said rotating axis, in order to vary the geometric phase and hence the measured interference from the detector, the measured varying interference being used by a processor to calculate the retardation and eigenpolarisation of the unknown retarding device.

* * * * *